(12) United States Patent
Hirano et al.

(10) Patent No.: US 8,137,852 B2
(45) Date of Patent: Mar. 20, 2012

(54) LIQUID ELECTROLYTE

(75) Inventors: Tetsuji Hirano, Ube (JP); Nobuharu Hisano, Ube (JP); Masayuki Kinouchi, Ube (JP)

(73) Assignee: Ube Industries, Ltd., Yamaguchi (JP)

( * ) Notice: Subject to any disclaimer, the term of this patent is extended or adjusted under 35 U.S.C. 154(b) by 1022 days.

(21) Appl. No.: 11/667,239

(22) PCT Filed: Nov. 8, 2005

(86) PCT No.: PCT/JP2005/020431
§ 371 (c)(1),
(2), (4) Date: May 8, 2007

(87) PCT Pub. No.: WO2006/051772
PCT Pub. Date: May 18, 2006

(65) Prior Publication Data
US 2007/0269710 A1 Nov. 22, 2007

(30) Foreign Application Priority Data

| Nov. 9, 2004 | (JP) | 2004-324669 |
| Sep. 12, 2005 | (JP) | 2005-263901 |
| Sep. 12, 2005 | (JP) | 2005-264277 |

(51) Int. Cl.
*H01M 8/06* (2006.01)

(52) U.S. Cl. ........ 429/409; 429/477; 429/479; 429/492; 429/499; 429/500

(58) Field of Classification Search .......... 429/409, 429/477, 479, 492, 499, 500, 188, 304, 305
See application file for complete search history.

(56) References Cited

U.S. PATENT DOCUMENTS

| 5,344,722 A | 9/1994 | Bjerrum et al. |
| 5,520,849 A * | 5/1996 | Eiffler ........................ 252/500 |
| 2002/0160272 A1 * | 10/2002 | Tanaka et al. .............. 429/314 |

FOREIGN PATENT DOCUMENTS

| EP | 520469 | 12/1992 |
| JP | 62-1215 | 1/1987 |
| JP | 62-1216 | 1/1987 |
| JP | 5-13278 | 1/1993 |
| JP | 5-258757 | 10/1993 |
| JP | 6-275297 | 9/1994 |
| JP | 8-88013 | 4/1996 |
| JP | 8-321439 | 12/1996 |
| JP | 8-180891 | 7/1997 |
| JP | 9-293523 | 11/1997 |

(Continued)

OTHER PUBLICATIONS

Imidazole and 1-methyl imidazole in phosphoric acid doped polybenzimidazole electrolyte for fuel cells, Solid State Ionics, 147(2002) pp. 181-187, Schechter et al.*
Imidazole and 1-methyl imidazole in phosphoric acid doped polybenzimidazole electrolyte for fuel cells, Solid State Ionics, 147(2002) pp. 181-187, Schehter et al.*

(Continued)

*Primary Examiner* — Patrick Ryan
*Assistant Examiner* — Ben Lewis
(74) *Attorney, Agent, or Firm* — Young & Thompson

(57) ABSTRACT

A liquid electrolyte composed of a base A and phosphoric acid B in a molar ratio A:B in a range of 1:3 to 1:50 having a solidification temperature of lower than −30° C.; and a composite electrolyte membrane comprising a porous body impregnated with such a liquid electrolyte.

5 Claims, 3 Drawing Sheets

FOREIGN PATENT DOCUMENTS

| | | |
|---|---|---|
| JP | 11-238521 | 8/1999 |
| JP | 2003-229333 | 8/2003 |
| JP | 2004-296275 | 10/2004 |
| JP | 2005-29497 | 2/2005 |
| JP | 2005-32531 | 2/2005 |
| JP | 2005-44550 | 2/2005 |
| JP | 2005-158646 | 6/2005 |
| WO | 2005/006352 | 1/2005 |

OTHER PUBLICATIONS (H. Ohno, ed) "Ionic Liquids: The Front and Future of Material Development" CMC Publishing Co., Ltd. 28-31 (2003).

"Functionalization and Application of Ionic Liquids" NTS Inc. 105-123 (2004).

J. Am. Chem. Soc. 47, 2165 (1925).

"The 35$^{th}$ Symposium on Molten Salt Chemistry" 81-82 (2003).

* cited by examiner

[Fig.1]
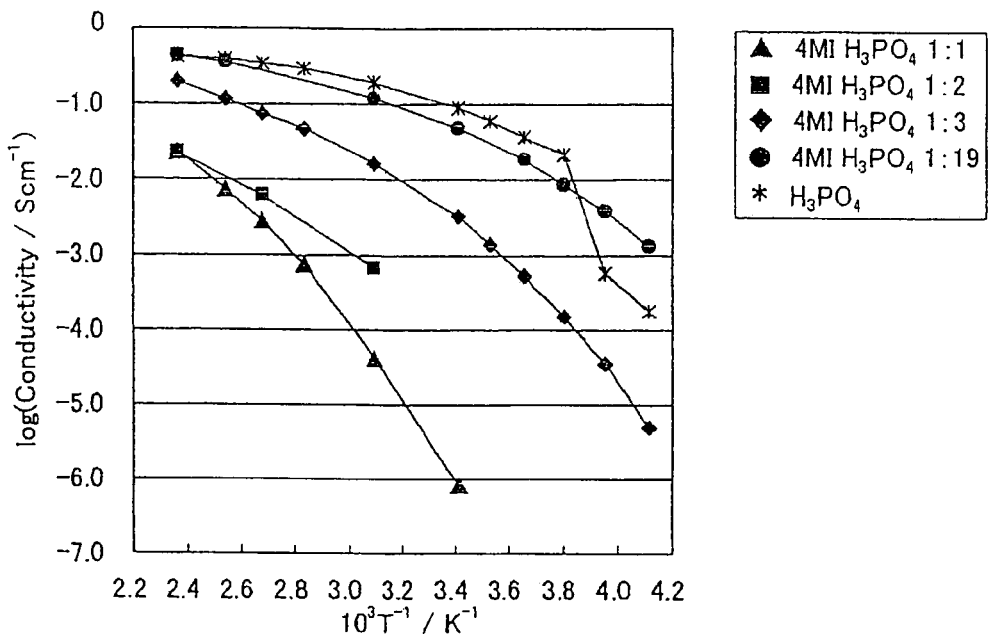
[Fig.2]
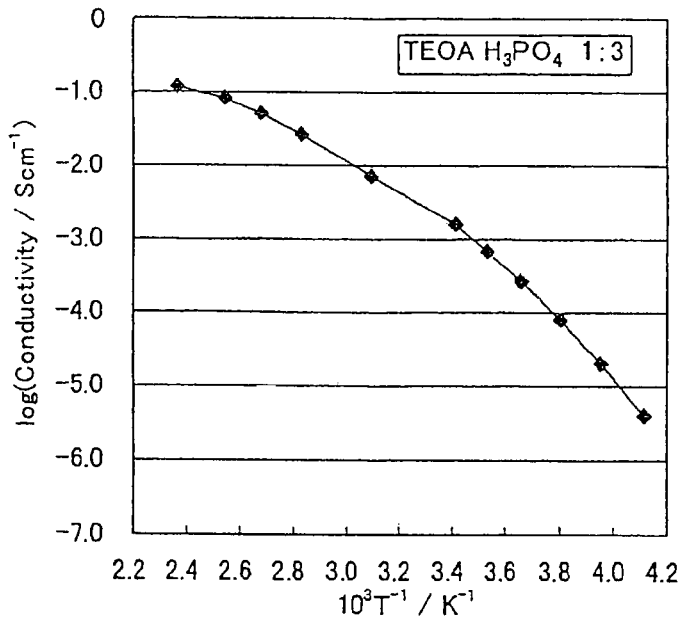

[Fig.3]
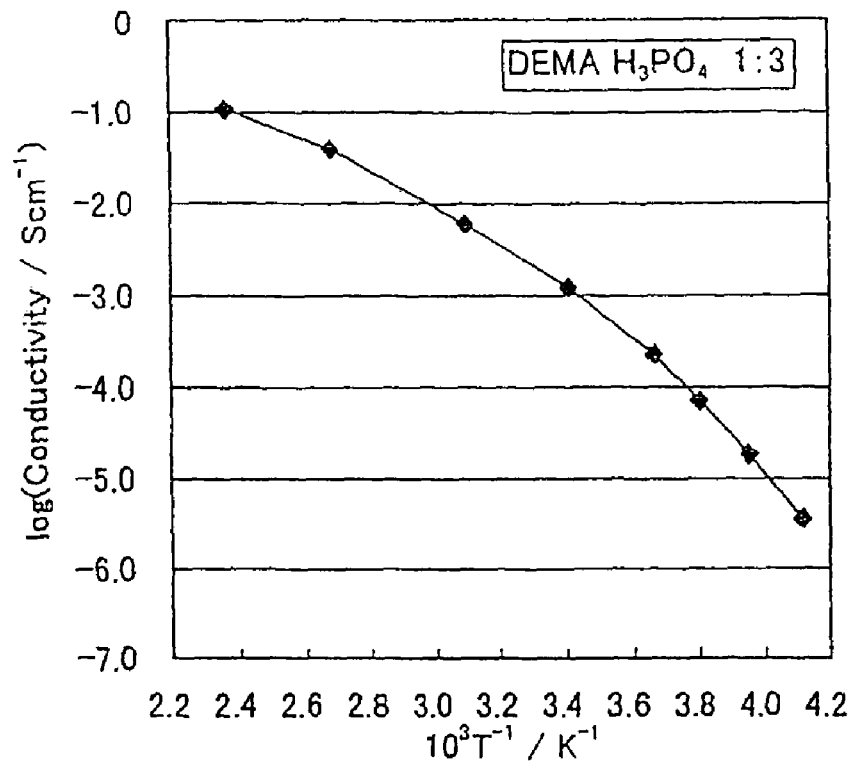
[Fig.4]
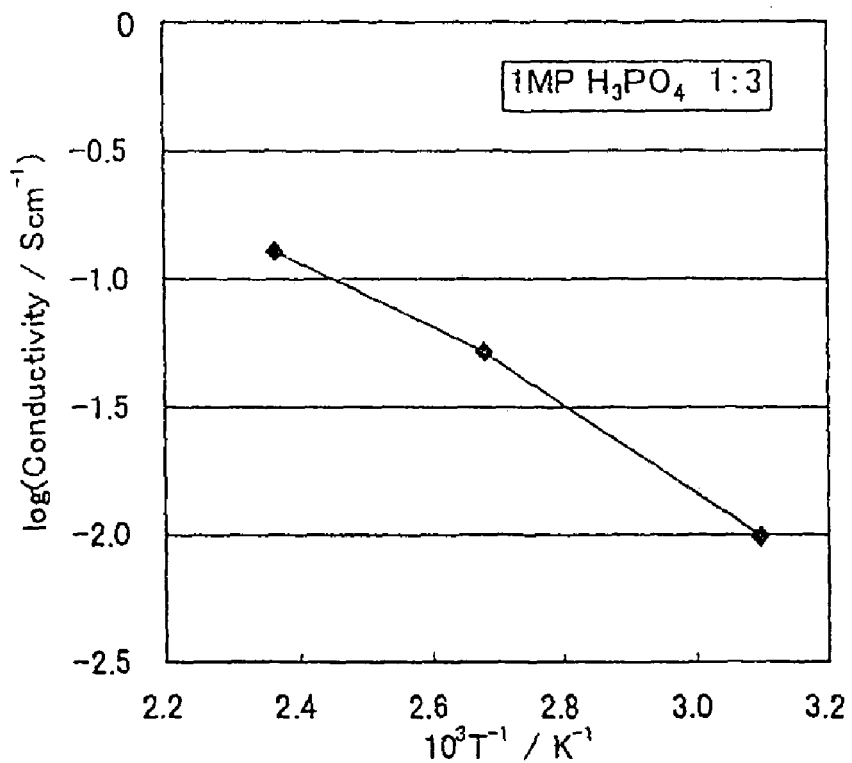

[Fig.5]
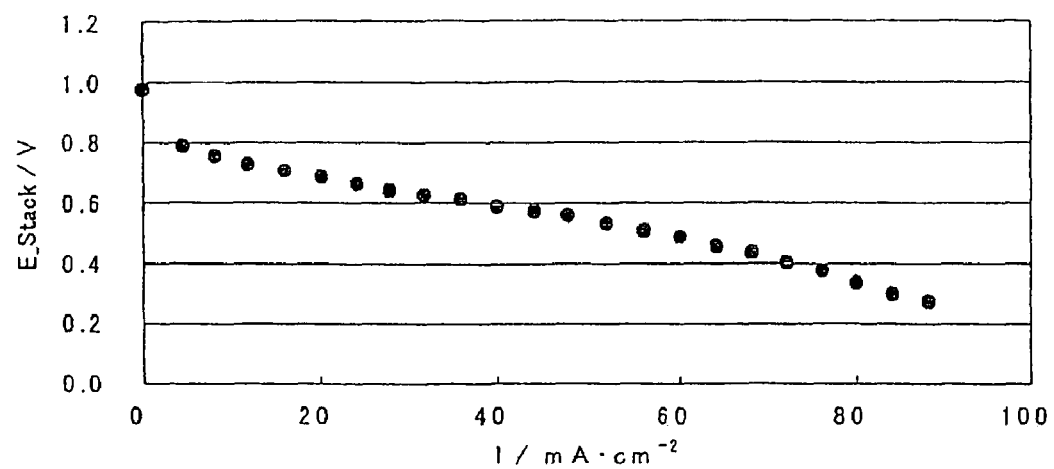

LIQUID ELECTROLYTE

FIELD OF THE INVENTION

The present invention relates to an electrolyte that is composed of a base and phosphoric acid, does not solidify at low temperature, and is liquid in a wide range of temperatures. More specifically, the present invention relates to a liquid electrolyte usable in fuel cells, secondary batteries, electrical double layer capacitors, electrolytic capacitors, and the like. The present invention also relates to a composite electrolyte membrane containing a porous body impregnated with the above liquid electrolyte. Further, the present invention relates to a fuel cell using the above liquid electrolyte or the above composite electrolyte membrane.

BACKGROUND ART

In electrochemical devices such as lithium ion batteries and electrical double layer capacitors, there is generally used an electrolyte containing a salt such as lithium salts and ammonium salts dissolved in an organic solvent such as propylene carbonate. However, there remains safety problem associated with volatility of such organic solvents.

It is known that some ammonium salts such as imidazolium salts and pyridinium salts liquefy to molten salt below 100° C., particularly around room temperature, and exhibit high ionic conductivity at relatively low temperatures below 200° C. without water or organic solvent added. These salts have been investigated for application as electrolytes for batteries and others owing to their characteristic involatility. As ionic liquids, many examples of N-substituted imidazolium salts and pyridinium salts are known (see Non-Patent Document 1).

A typical organic solvent electrolyte for electrical double layer capacitors includes an electrolyte containing an ammonium salt such as tetraethylammonium tetrafluoroborate dissolved in a polar solvent such as propylene carbonate. However, the ammonium salts are precipitated at low temperatures, causing a problem of lowering the capacity and conductivity. Accordingly, improving the performances at low temperatures is a critical problem to be solved (see Non-Patent Document 2).

There are examples of applying electrolytes consisting only of ionic liquid to electrical double layer capacitors, but such capacitors have a problem that the ionic liquid solidifies or if not solidify, becomes viscous, significantly decreasing the ionic conductivity at low temperatures below room temperature (see Non-Patent Document 2).

There is reported an example of an electrolyte where an ionic liquid is dissolved in an organic solvent, which shows improved low-temperature performances as compared with conventional electrolytes where an ammonium salt is dissolved in an organic solvent. However, the use of organic solvent poses problems in volatility and safety (see Non-Patent Document 2).

In a phosphoric acid fuel cell, phosphoric acid with a concentration of 85% by weight or more is generally used as an electrolyte. According to Non-Patent Document 3, the melting point of phosphoric acid with 100% purity is about 40° C., while phosphoric acid with a purity of 91.6% by weight or higher completely solidifies at 23.5° C. or lower temperatures. At a purity of 91.6% by weight or lower, solid and liquid co-exist at 20° C. or lower temperatures. Therefore, at an outside air temperature of 20° C. or lower, phosphoric acid solidifies in a phosphoric acid fuel cell out of service, and hence pre-melting of phosphoric acid with heating is required on restarting. Also, on transporting the phosphoric acid fuel cell to an installation site after production, the cell is required to be kept warm with an additional heating device for preventing solidification of phosphoric acid. In addition, solidification of phosphoric acid accompanies with volume change, thereby loading stress to the fuel cell, possibly resulting in degradation. For these reasons, preventing solidification of phosphoric acid is one of the problems of phosphoric acid fuel cells.

Patent Document 1 discloses a method for providing a fuel cell that can prevents complete solidification of the electrolyte during out-of-service period without using heating devices or wetting gas generators. However, phosphoric acid partially solidifies, thereby the resistance of the electrolyte is high on restarting the fuel cell.

Patent Document 2 discloses a method for operating a phosphoric acid fuel cell in which the solidification of phosphoric acid is suppressed on storage of the cell to enable restarting even when the cell temperature lowers to the outside air temperature after the operation is terminated. However, there are still problems of partial solidification of phosphoric acid and decrease in the fuel cell output due to the necessity of lowering operation temperatures.

Patent Document 3 discloses a noticeable method for transporting fuel cells with high reliability and low transporting cost, in which fuel cell degradation caused by solidification of phosphoric acid can be easily and surely avoided. However, phosphoric acid is required to be diluted by supplying and discharging wetting gas or to be re-concentrated by supplying and discharging drying gas. In addition, there remain problems in transportation or termination in extremely cold areas because phosphoric acid is frozen at −17° C. even when diluted to 75% by weight.

Non-Patent Document 4 discloses a normal-temperature molten salt of acid-excess type containing butylamine and phosphoric acid, but gives no specific description on its state and properties at low temperatures.

Patent Document 4 discloses an ionic liquid containing phosphoric acid and a cyclic organic base but does not resolve the above problems, since no description is given on whether the ionic liquid remains liquid or not below 20° C.

On the other hand, since liquid electrolytes are not easy to handle, it is publicly known to impregnate a porous body with a liquid electrolyte to improve the handleability. For example, Patent Documents 4, 5, and 6 disclose electrolyte membranes in which a porous membrane is impregnated with an electrolyte containing phosphoric acid or an electrolyte containing phosphoric acid and an organic solvent not forming a salt with phosphoric acid. However, the problem of low-temperature solidification is still unresolved.

Patent Document 1: Japanese Patent Laid-Open Publication No. H11-238521
Patent Document 2: Japanese Patent Laid-Open Publication No. H6-275297
Patent Document 3: Japanese Patent Laid-Open Publication No. H9-293523
Patent Document 4: Japanese Patent Laid-Open Publication No. 2005-44550
Patent Document 5: Japanese Patent Laid-Open Publication No. H8-88013
Patent Document 6: Japanese Patent Laid-Open Publication No. H8-180891
Non-Patent Document 1: "Ionsei ekitai no kinou sousei to ouyou (Ionic Liquids: The Front and Future of Material Development)" edited by Hiroyuki Ohno, CMC Publishing Co., Ltd., 28-31 (2003)

Non-Patent Document 2: "Functionalization and Application of Ionic Liquids" NTS Inc., 105-123 (2004)
Non-Patent Document 3: J. Am. Chem. Soc., 47, 2165 (1925)
Non-Patent Document 4: "The 35th Symposium on Molten Salt Chemistry" 81-82 (2003).

DISCLOSURE OF THE INVENTION

It is an object of the present invention to provide a novel liquid electrolyte that comprises a base and phosphoric acid and does not solidify at low temperatures.

It is an another object of the present invention to provide a novel composite electrolyte membrane free from low-temperature solidification with improved handleability by impregnating a porous body with a liquid electrolyte comprising a base and phosphoric acid.

The present invention relates to a liquid electrolyte comprising a base A and phosphoric acid B in a molar ratio, A:B, in the range of 1:3 to 1:50 having a solidification temperature lower than −30° C.

The present invention also relates to the above liquid electrolyte whose ionic conductivity is $10^{-6}$ Scm$^{-1}$ or more at −30° C.

The present invention also relates to the above liquid electrolyte whose ionic conductivity is $10^{-2}$ Scm$^{-1}$ or more at 150° C.

The present invention also relates to the above liquid electrolyte, wherein the base is an amine.

The present invention also relates to the above liquid electrolyte, wherein the base is an imidazole represented by chemical formula (1) below:

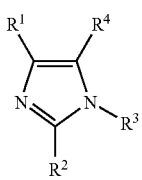
(1)

[In the formula, $R^1$, $R^2$, $R^3$, and $R^4$ each independently represent a hydrocarbon group having 1 to 20 carbon atoms or hydrogen atom.]

The present invention relates to the above liquid electrolyte, wherein the base is an amine represented by chemical formula (2) below:

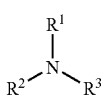
(2)

[In the formula, $R^1$, $R^2$, and $R^3$, each independently represent a hydrocarbon group having 1 to 20 carbon atoms, hydroxyl-containing hydrocarbon group having 1 to 20 carbon atoms, or hydrogen atom; and at least one of $R^1$, $R^2$, and $R^3$ is the hydrocarbon group or hydroxyl-containing hydrocarbon group.]

The present invention relates to the above liquid electrolyte, wherein the base is a pyrrolidine represented by chemical formula (3) below:

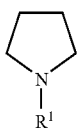
(3)

[In the formula, $R^1$ represents a hydrocarbon group having 1 to 20 carbon atoms or hydrogen atom.]

The present invention relates to the above liquid electrolyte that is a proton conductor.

In addition, the present invention relates to a composite electrolyte membrane comprising in a porous body impregnated with the above liquid electrolyte.

The present invention also relates to a fuel cell using the above liquid electrolyte or composite electrolyte membrane.

BRIEF DESCRIPTION OF THE DRAWINGS

FIG. 1 illustrates the temperature dependence of the ionic conductivity for 4MI/H$_3$PO$_4$ (1:1, 1:2, 1:3, and 1:19) in Example 1, and phosphoric acid in Comparative Example 1.

FIG. 2 illustrates the temperature dependence of the ionic conductivity for TEOA/H$_3$PO$_4$ 1:3 in Example 4.

FIG. 3 illustrates the temperature dependence of the ionic conductivity for DEMA/H$_3$PO$_4$ 1:3 in Example 6.

FIG. 4 illustrates the temperature dependence of the ionic conductivity for 1MP/H$_3$PO$_4$ 1:3 in Example 10.

FIG. 5 illustrates the relationship between the output voltage and current for the power generation with a fuel cell using 4MI-H$_3$PO$_4$ 1:19 liquid electrolyte in Example 11.

BEST MODE FOR CARRYING OUT THE INVENTION

The liquid electrolyte of the present invention comprises a base and phosphoric acid, and its solidification temperature is preferably lower than −30° C. more preferably lower than −40° C., and still more preferably lower than −50° C. Solidification temperatures exceeding the above temperature are not preferred, since the electrolyte may solidify in extremely cold areas.

In the present invention, "solidification" means the phenomenon that liquid becomes solid, including "crystallization" and "vitrification." Depending on conditions, solidification may refer to conversion to a state where solid and liquid co-exist or a state where crystalline part and non-crystalline part co-exist, as far as the substance substantially loses fluidity as liquid state. In the present invention, "liquid" may be supercooled state.

For the liquid electrolyte of the present invention, the time required for solidification at low temperatures is preferably not shorter than half a day, that is, 12 hours, more preferably one day or more, still more preferably one week or more, and particularly preferably one month or more. The liquid electrolyte preferably does not solidify on a semipermanent base. Solidification time shorter than the above is not preferred, since the liquid electrolyte may solidify during out-of-service period in electrochemical devices to which the electrolyte is applied.

The molar ratio of the base and phosphoric acid, which are the constituents of the liquid electrolyte of the present invention, is in the range of 1:3 to 1:50, preferably 1:3 to 1:40, more preferably 1:3 to 1:30, still more preferably 1:3 to 1:20, and particularly preferably 1:5 to 1:20. It is unfavorable that the ratio of the base to phosphoric acid is outside of 1:3 to 1:50 described above because of increase in the solidification temperature or viscosity.

The ionic conductivity of the liquid electrolyte of the present invention is preferably $1\times10^{-6}$ Scm$^{-1}$ or more, and more preferably $1\times10^{-3}$ Scm$^{-1}$ or more, at a temperature as low as −30° C. The ionic conductivity lower than the above value is unfavorable, because use of the liquid electrolyte is impractical in cold climates.

The ionic conductivity of the liquid electrolyte of the present invention is preferably $1\times10^{-2}$ Scm$^{-1}$ or more, and more preferably $1\times10^{-1}$ Scm$^{-1}$ or more, at 150° C. The ionic conductivity lower than the above value is unfavorable because of higher resistance in use at high temperatures.

The base composing the liquid electrolyte of the present invention is preferably an amine. Preferred amines include imidazoles, aliphatic amines, aromatic amines, amines substituted with (a) hydroxyl-containing alkyl group(s), pyrrolidines, and others. The amine may be a heterocyclic amine other than imidazoles or pyrrolidines, including azoles such as pyrazoles, triazoles, oxazoles, and thiazoles, pyridines, pyrazines, pyrroles, piperidines, and others.

In terms of lowering the solidification temperature, preferred are imidazoles, aliphatic tertiary amines, amines substituted with (a) hydroxyl-containing alkyl group(s), and pyrrolidines.

Preferred imidazoles are represented by chemical formula (1) below.

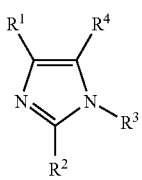

(1)

In formula (1), it is preferred that each of $R^1$, $R^2$, $R^3$, and $R^4$ is independently a hydrocarbon group having 1 to 20 carbon atoms or hydrogen atom.

In addition, preferably, at least one of $R^1$, $R^2$, $R^3$, and $R^4$ is a hydrocarbon group having 1 to 20 carbon atoms.

Examples of the hydrocarbon group having 1 to 20 carbon atoms represented by $R^1$, $R^2$, $R^3$, or $R^4$ include linear groups such as methyl, ethyl, n-propyl, n-butyl, hexyl, and octyl; branched groups such as isopropyl, s-butyl, and t-butyl; alicyclic groups such as cyclohexyl; aromatic groups such as phenyl; and others. In particular, methyl, ethyl, n-propyl, and n-butyl are preferable.

Specifically, the imidazoles include imidazole; 4-substituted imidazoles such as 4-methylimidazole, 4-ethylimidazole, and 4-phenylimidazole; 2-substituted imidazoles such as 2-methylimidazole, 2-ethylimidazole, and 2-phenylimidazole; 2,4-disubstituted imidazoles such as 2-ethyl-4-methylimidazole, 2-cyclohexyl-4-methylimidazole, 2-octyl-4-hexylimidazole, 2-ethyl-4-phenylimidazole, and 2-butyl-4-allylimidazole; 1-alkylimidazoles such as 1-methylimidazole, 1-ethylimidazole, 1-propylimidazole, 1-butylimidazole, 1-hexylimidazole, and 1-octylimidazole; benzimidazoles such as benzimidazole and 1-methylbenzimidazole; and others. Among these, nonsymmetrical imidazoles such as 4-substituted imidazoles and 2,4-disubstituted imidazoles, and 1-alkylimidazoles, which are N-substituted, are preferable, because they provide larger inhibitory effects on the solidification.

Amines represented by chemical formula (2) below are also preferable.

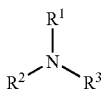

(2)

In formula (2), $R^1$, $R^2$, and $R^3$ each independently represent a hydrocarbon group having 1 to 20 carbon atoms, hydroxyl-containing hydrocarbon group having 1 to 20 carbon atoms, or hydrogen atom, and preferably at least one of $R^1$, $R^2$, and $R^3$ is the hydrocarbon group or hydroxyl-containing hydrocarbon group.

Further, it is preferred that all of $R^1$, $R^2$, and $R^3$ are hydrocarbon groups having 1 to 20 carbon atoms.

When two or more of $R^1$, $R^2$, and $R^3$ are hydrocarbon groups, they are preferably two or more different hydrocarbon groups.

The hydrocarbon group having 1 to 20 carbon atoms represented by $R^1$, $R^2$, or $R^3$ includes groups listed above for chemical formula (1). In particular, methyl, ethyl, n-propyl, and n-butyl are preferable. The hydroxyl-containing hydrocarbon group includes substituents corresponding to primary alcohols such as —CH$_2$OH, —CH$_2$CH$_2$OH, and —CH$_2$CH$_2$CH$_2$OH; substituents corresponding to secondary alcohols such as —CH$_2$CH(OH)CH$_3$; substituents corresponding to tertiary alcohols such as —CH$_2$C(OH)(CH$_3$)$_2$. Among these, —CH$_2$OH and —CH$_2$CH$_2$OH are preferable.

The aliphatic amines include, specifically, primary amines such as methylamine, ethylamine, propylamine, butylamine, s-butylamine, t-butylamine, hexylamine, cyclohexylamine, and octylamine; secondary amines such as dimethylamine, diethylamine, N-ethylmethylamine, N-methylpropylamine, N-methylbutylamine, N-methyl-t-butylamine, and N-methylcyclohexylamine; and tertiary amines such as trimethylamine, triethylamine, N,N-dimethylethylamine, N,N-diethylmethylamine, and N,N-dimethylcyclohexylamine. Among these, tertiary amines having different substituents such as N,N-dimethylethylamine, N,N-diethylmethylamine, and N,N-dimethylcyclohexylamine are preferable, because the solidification temperature is lowered.

The aromatic amines include anilines such as aniline and N-methylaniline; phenylenediamines such as 1,2-phenylenediamine, 1,3-phenylenediamine, and 1,4-phenylenediamine; phenylenediamines such as N-methyl-1,2-phenylenediamine; aminonaphthalenes such as 1-aminonaphthalene and 2-aminonaphthalene; diaminonaphthalenes such as 1,5-diaminonaphthalene and 1,8-diaminonaphthalene; and others.

Amines substituted with (a) hydroxyl-containing alkyl group(s) are also preferably used.

Specifically, such compounds include monoalcoholamines such as methanolamine and ethanolamine; dialcoholamines such as dimethanolamine, methyldiethanolamin, n-butyldiethanolamine, s-butyldiethanolamine and t-butyldiethanolamine; trialcoholamines such as trimethanolamine and triethanolamine; and others. Among these, triethanolamine, methyldiethanolamine, and n-butyldiethanolamine are preferable.

Preferred pyrrolidines are represented by chemical formula (3) below.

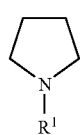

(3)

In formula (3), $R^1$ represents a hydrocarbon group having 1 to 20 carbon atoms or hydrogen atom.

Specifically, the pyrrolidines include, besides pyrrolidine, 1-alkylpyrrolidines such as 1-methylpyrrolidine and 1-ethylpyrrolidine. Among these, 1-methylpyrrolidine is preferable.

The azoles other than imidazoles include pyrazoles such as pyrazole, 1-methylpyrazole, 3-methylpyrazle, and 4-methylpyrazole; triazoles such as triazole; oxazoles such as oxazole; thiazoles such as thiazole; and others.

The pyridines include, besides pyridine, alkylpyridines such as 2-ethylpyridine, 3-ethylpyridine, 4-ethylpyridine, 3-butylpyridine, and 4-t-butylpyridine; dialkylpyridines such as 2,4-lutidine, 2,3-lutidine, 2,6-lutidine, and 3,4-lutidine; and others.

The pyrazines include, besides pyrazine, 2-alkylpyrazines such as 2-methylpyrazine and 2-ethylpyrazine.

The pyrroles include, besides pyrrole, 1-alkylpyrroles such as 1-methylpyrrole and 1-ethylpyrrole, and others.

The piperidines include, beisdes piperidine, 1-alkylpiperidines such as 1-methylpiperidine and 1-ethylpiperidine; 2-alkylpiperidines such as 2-methylpiperidine and 2-ethylpiperidine; and others.

The above base component may be a mixture of two or more compounds. For example, as a mixture of two compounds, there may be mentioned a combination of 1-ethylimidazole and 4-methylimidazole, 1-ethylimidazole and 2-ethyl-4-methylimidazole, 4-methylimidazole and 2-ethylimidazole, 4-methylimidazole and 2-ethyl-4-methylimidazole, N,N-diethylmethylamine and 4-methylimidazole, N,N-dimethylcyclohexylamine and 4-methylimidazole, N,N-diethylmethylamine and N,N-dimethylcyclohexylamine, triethanolamine and 4-methylimidazole, triethanolamine and diethylmethylamine, triethanolamine and N,N-dimethylcyclohexylamine, or the like.

The liquid electrolyte of the present invention may be a proton conductor. The liquid electrolyte with proton conductivity can be preferably used for fuel cells.

The phosphoric acid used in the present invention may be any of orthophosphoric acid, pyrophosphoric acid, metaphosphoric acid, and their mixtures. Since condensed phosphoric acid is highly viscous and is not easy to handle, orthophosphoric acid is preferably used.

The heat resistance of the liquid electrolyte of the present invention is preferably 150° C. or higher, more preferably 180° C. or higher, and still more preferably 200° C. or higher. Heat resistance lower than the above temperature is unfavorable, because use of such electrolyte lowers the performances of devices operating at high temperatures such as phosphoric acid fuel cells.

The liquid electrolyte of the present invention may contain water or an organic solvent. The organic solvent includes polar solvents such as ethylene carbonate, propylene carbonate, butylene carbonate, acetonitrile, N,N-dimethylformamide, N,N-dimethylacetamide, N,N-dimethylimidazolidinone, N-methyl-2-pyrrolidone, γ-valerolactone, sulfolane, acetone, methanol, ethanol, 1-propanol, and 2-propanol.

The liquid electrolyte of the present invention, which comprises a base and phosphoric acid, does not solidify at low temperatures, exhibits high ionic conductivity at both low and high temperatures without water or solvent added, and hence can be suitably used for fuel cells, secondary batteries, electrical double layer capacitors, electrolytic capacitors, and the like.

In a use of the liquid electrolyte of the present invention, a porous body may be impregnated with said liquid electrolyte. The porous body includes sintered bodies, non-woven fabrics, woven fabrics, and microporous membranes made of an inorganic compound including glass, silica, and metal oxides such as alumina, zirconium oxide, and titanium oxide, or a polymer such as rayon, polyolefin, polyester, polyamide, fluororesin, polyimide, polyether, polysulfide, polyarylene, polybenzazole, polyquinoxaline, and polystyrene.

The composite electrolyte membrane of the present invention comprises a porous body impregnated with the liquid electrolyte of the present invention.

The form of porous body used in the present invention is a sintered body, non-woven fabric, woven fabric, or microporous membrane. The thickness of the porous body is preferably from 1 μm to 500 μm, and particularly preferably from 5 μm to 450 μm. A porous body thinner than 1 μm is undesirable because of poor strength of the resulting membrane, while thickness exceeding 500 μm is also undesirable because of lowering in the conductivity. The porosity of the porous body is preferably from 20% to 95%, and particularly preferably from 30% to 90%. Porosity lower than 20% is unfavorable because of lowering in the conductivity, while porosity exceeding 95% is also unfavorable because of lowering in strength of the membrane. The average pore diameter of penetrating pores is selected from such a range that the liquid electrolyte can be retained therein, but it is preferably from 0.1 μm to 1000 μm, and particularly preferably from 0.2 μm to 750 μm. Diameters less than 0.1 μm are undesirable because of difficulty in impregnation of the liquid electrolyte, while diameters larger than 1000 μm is also undesirable because of increased possibility of leakage of the liquid electrolyte.

The material for porous body used in the present invention may be an inorganic compound including glass, silica, and metal oxides such as alumina, zirconium oxide, and titanium oxide, or a polymer such as rayon, polyolefin, polyester, polyamide, fluororesin, polyimide, polyether, polysulfide, polyarylene, polybenzazole, polyquinoxaline, and polystyrene. Among these, polymers with a glass transition temperature of 100° C. or higher and the above inorganic compounds are preferable, considering power generation efficiency of fuel cells and operation temperatures of 100° C. or higher. In terms of oxidation resistance, preferred polymers are aromatic polymers including aromatic polyimides such as polyimide and polyetherimide; polysulfone, aromatic polyethers such as polyethersulfone, polyphenyleneoxide, polyetherketone, polyetheretherketone, and polyetheretherketoneketone; aromatic polysulfides such as poly(phenylene sulfide); polybenzazoles such as polybenzimidazole, polybenzoxazole, and polybenzthiazole; and polyquinoxalines such as polyquinoxaline and polyphenylquinoxaline.

In the present invention, the porous body can be impregnated with the liquid electrolyte using publicly known methods. For example, (1) the porous body is immersed in the liquid electrolyte so that the liquid electrolyte is incorporated into the pores of the porous body and retained therein; and if necessary, (2) the liquid electrolyte is made to permeate the porous body while degassing under reduced pressure or pressurizing so as to replace gas inside the pores of the porous body by the liquid electrolyte and to retain the liquid electrolyte inside the pores.

In methods (1) and (2) above, impregnation may be conducted using a solution of the liquid electrolyte in a solvent that does not dissolve the porous body. In this case, only the solvent can be evaporated by heating after the impregnation.

There may be used any solvent that does not substantially dissolve the porous body without particular limitations. Examples of the solvent include amides, sulfones, alcohols, ethers, ketones, and others. Specifically, preferably used are water, N,N-dimethylformamide, N,N-dimethylacetamide, N-methyl-2-pyrrolidone, 1,3-dimethyl-2-imidazolidinone, dimethylsulfoxide, sulfolane, diphenyl sulfone, tetrahydrofuran, methanol, ethanol, isopropyl alcohol, ethylene glycol monomethyl ether, ethylene glycol monoethyl ether, propylene glycol monomethyl ether, diethyl ether, acetone, and others.

The impregnation of the liquid electrolyte or a solution thereof into the porous body may be performed at any temperature that is not lower than melting point of the liquid electrolyte or the solvent, not higher than the boiling point of the solvent, below the melting or decomposition point of the porous body, and below the decomposition point of the liquid electrolyte, without particular limitations. For example, the temperature in impregnation may be 0° C. to 300° C.

In the present invention, a surfactant may be used to facilitate the impregnation of the liquid electrolyte into the porous body.

The fuel cell of the present invention uses the above liquid electrolyte or composite electrolyte membrane of the present invention and may be configured using known components for conventional phosphoric acid fuel cells or solid polymer fuel cells except the liquid electrolyte or composite electrolyte membrane. For example, the fuel cell has a configuration in which a porous body made of an inorganic compound or polymer impregnated with the liquid electrolyte, such as the above composite electrolyte membrane, is sandwiched between a pair of porous gas diffusion electrodes composed of a catalyst such as platinum loaded on carbon fine particles or fibers, and each side of the sandwiched assembly is provided with a separator made of conductive carbon or metal with fuel-gas conduits. For the fuel cell of the present invention, the usual operation temperature is 20° C. to 250° C., preferably 30° C. to 240° C., and more preferably 40° C. to 230° C. Operation below 20° C. is unfavorable because of lowering in the power generation efficiency, while operation above 250° C. is also unfavorable due to occurrence of decomposition or the like.

EXAMPLES

Hereinafter, the present invention will be specifically explained through Examples and Comparative Examples. The observed values given in Examples and Comparative Examples were obtained by the following methods.
1) Observation of State of Electrolyte at −30° C.

Approximately 2 g of a dried sample was put in a sample bottle, and the bottle was tightly sealed and kept at 60° C. for 2 hours and at 25° C. overnight in a thermostatted bath. After that, the sample bottle was stood still at −30° C., and the sample was observed to examine whether it solidified or not at every predetermined time.
2) Ionic Conductivity Measurement for Electrolyte A dried sample was put in a sample bottle, platinum plates 2 cm long and 1.5 cm wide were immersed in parallel to each other with a spacing of 1 cm in the sample, and the sample bottle was tightly sealed to form a cell for conductivity measurement. In a thermostatted bath at a predetermined temperature, the ionic conductivity was determined by the complex impedance measurement with FRD1025 and Potentiostat/Galvanostat 283 manufactured by Princeton Applied Research.
3) Ionic Conductivity Measurement for Composite Electrolyte Membrane A composite electrolyte membrane was sandwiched between platinum discs having a diameter of 13 mm. In a thermostatted bath at a predetermined temperature, the ionic conductivity of the composite electrolyte membrane was determined by the complex impedance measurement with FRD1025 and Potentiostat/Galvanostat 283 manufactured by Princeton Applied Research.

Example 1

4-Methylimidazole/phosphoric acid (4MI/$H_3PO_4$)

In a glove box under a nitrogen atmosphere, liquid phosphoric acid obtained by melting crystalline phosphoric acid (Aldrich) and 4-methylimidazole (4MI; Aldrich) were mixed in predetermined amounts to obtain liquid electrolytes with various molar ratios. The molar ratios of 4MI and phosphoric acid in the mixtures were 1:1, 1:2, 1:3, 1:4, 1:5, 1:6, 1:7, 1:8, 1:9, 1:10, 1:11, 1:13, 1:15, 1:19, 1:24, 1:34, 1:49, and 1:99. When the mixture did not become a homogeneous liquid, it was heated in a hot-air constant-temperature oven at 50° C. or an oil bath at 120° C. to make a homogeneous liquid. The observation results of the state at −30° C. are shown in Table 1. The electrolytes with molar ratios of 1:3 to 1:24 remained liquid for at least 70 days at a temperature as low as −30° C. The 1:34 mixture solidified after 10 days, the 1:49 mixture solidified after 24 days, and the 1:99 mixture solidified after one day. The temperature dependences of the ionic conductivity for 4MI/$H_3PO_4$ with molar ratios of 1:1, 1:2, 1:3, and 1:19 are shown in FIG. 1. The ionic conductivities of 4MI/$H_3PO_4$ 1:3 were $4.9 \times 10^{-6}$ Scm$^{-1}$ at −30° C. and $2.0 \times 10^{-1}$ S/cm$^{-1}$ at 150° C. The ionic conductivities of 4MI/$H_3PO_4$ 1:19 were $1.3 \times 10^{-3}$ Scm$^{-1}$ at −30° C. and $4.3 \times 10^{-1}$ S/cm$^{-1}$ at 150° C. While the ionic conductivity of phosphoric acid in Comparative Example 1 below drastically decreased with the solidification at low temperatures, 4MI-$H_3PO_4$ 1:19 did not solidify and retained a high ionic conductivity.

Example 2

N-Ethylimidazole/phosphoric acid (1EI/$H_3PO_4$)

Liquid electrolytes with various molar ratios were prepared similarly to Example 1 except that N-ethylimidazole (1EI; Tokyo Chemical Industry Co., Ltd.) was used instead of 4MI. The observation results of the state at −30° C. are shown in Table 1. The electrolytes with molar ratios of 1:3 to 1:24 and 1:49 remained liquid for at least 44 days at a temperature as low as −30° C.

Example 3

N,N-Dimethylcyclohexylamine/phosphoric acid (DMCA/$H_3PO_4$)

Liquid electrolytes with various molar ratios were prepared similarly to Example 1 except that N,N-dimethylcyclohexylamine (DMCA; Wako Pure Chemical Industries, Ltd.) was used instead of 4MI. The observation results of the state at −30° C. are shown in Table 1. The electrolytes with molar ratios of 1:3 to 1:34 remained liquid for at least 65 days at a temperature as low as −30° C.

Example 4

Triethanolamine/phosphoric acid (TEOA/$H_3PO_4$)

Liquid electrolytes with various molar ratios were prepared similarly to Example 1 except that triethanolamine (TEOA; Sigma-Aldrich Japan K.K.) was used instead of 4MI. The observation results of the state at −30° C. are shown in Table 1. The electrolytes with molar ratios of 1:3 to 1:24 and 1:49 remained liquid for at least 69 days at a temperature as low as −30° C. The temperature dependence of the ionic conductivity for TEOA/H$_3$PO$_4$ 1:3 is shown in FIG. 2. The ionic conductivities of TEOA/H$_3$PO$_4$ 1:3 were $4.0 \times 10^{-6}$ Scm$^{-1}$ at −30° C. and $1.2 \times 10^{-1}$ Scm$^{-1}$ at 150° C.

Example 5

Butylamine/phosphoric acid (BA/H$_3$PO$_4$)

Liquid electrolytes with various molar ratios were prepared similarly to Example 1 except that butylamine (BA; Aldrich) was used instead of 4MI. The observation results of the state at −30° C. are shown in Table 1. The electrolytes with molar ratios of 1:2 to 1:19, 1:34, and 1:49 remained liquid for at least 65 days at a temperature as low as −30° C.

Example 6

N,N-Diethylmethylamine/phosphoric acid (DEMA-H$_3$PO$_4$)

A liquid electrolyte with a molar ratio of 1:3 was prepared similarly to Example 1 except that N,N-diethylmethylamine (DEMA; Tokyo Chemical Industry, Co., Ltd.) was used instead of 4MI. DEMA/H$_3$PO$_4$ 1:3 remained liquid for at least 117 days at −30° C. The temperature dependence of the ionic conductivity for DEMA/H$_3$PO$_4$ 1:3 is shown in FIG. 3. The ionic conductivities of DEMA/H$_3$PO$_4$ 1:3 were $3.5 \times 10^{-6}$ Scm$^{-1}$ at −30° C. and $1.1 \times 10^{-1}$ Scm$^{-1}$ at 150° C.

Example 7

N-Methyldiethanolamine/phosphoric acid (MDEOA/H$_3$PO$_4$)

A liquid electrolyte with a molar ratio of 1:3 was prepared similarly to Example 1 except that N-methyldiethanolamine (MDEOA; Aldrich) was used instead of 4MI. MDEOA/H$_3$PO$_4$ 1:3 remained liquid for at least 125 days at −30° C.

Example 8

2,2'-(Butylimino)diethanolamine/phosphoric acid (BDEOA/H$_3$PO$_4$)

A liquid electrolyte with a molar ratio of 1:3 was prepared similarly to Example 1 except that 2,2'-(butylimino)diethanolamine (BDEOA; Tokyo Chemical Industry Co., Ltd.) was used instead of 4MI. BDEOA/H$_3$PO$_4$ 1:3 remained liquid for at least 117 days at −30° C.

Example 9

2-Ethyl-4-methylimidazole/phosphoric acid (2E4MZ/H$_3$PO$_4$)

A liquid electrolyte with a molar ratio of 1:3 was prepared similarly to Example 1 except that 2-ethyl-4-methylimidazole (2E4MZ; Shikoku Chemicals Corporation) was used instead of 4MI. 2E4MZ/H$_3$PO$_4$ 1:3 remained liquid for at least 112 days at −30° C.

Example 10

1-Methylpyrrolidine/phosphoric acid (1MP/H$_3$PO$_4$)

A liquid electrolyte with a molar ratio of 1:3 was prepared similarly to Example 1 except that 1-methylpyrrolidine (1MP; Tokyo Chemical Industry Co., Ltd.) was used instead of 4MI. 1MP/H$_3$PO$_4$ 1:3 remained liquid for at least one week at −30° C. The temperature dependence of the ionic conductivity for 1MP/H$_3$PO$_4$ 1:3 is shown in FIG. 4. The ionic conductivity of 1MP/H$_3$PO$_4$ 1:3 was $1.3 \times 10^{-1}$ Scm$^{-1}$ at 150° C.

Comparative Example 1

Phosphoric Acid

When crystalline phosphoric acid was melt with heating at 60° C., and the liquid was kept still at −10° C., it solidified in 2 hours. The temperature dependence of the ionic conductivity for phosphoric acid is shown in FIG. 1. The ionic conductivity drastically decreased when phosphoric acid solidified at a temperature between −10° C. and −20° C.

Example 11

Power Generation Test of Fuel Cell

Power generation was tested at a cell temperature of 120° C. for a fuel cell using the liquid electrolyte 4MI/H$_3$PO$_4$ 1:19 prepared in Example 1. The result is shown in FIG. 5. In the power generation test, a phosphoric acid fuel cell FC-02PA and an electrode-matrix assembly FC25-PA/EM manufactured by Electrochem, Inc., were used. Non-humidified hydrogen gas at 150 ml/min and oxygen gas at 150 ml/min were supplied as fuel-gases.

TABLE 1

Table 1
Observation results of state

| Molar ratio Base:Phosphoric acid | Example 1 4MI/H$_3$PO$_4$ | Example 2 1EI/H$_3$PO$_4$ | Example 3 DMCA/H$_3$PO$_4$ | Example 4 TEOA/H$_3$PO$_4$ | Example 5 BA/H$_3$PO$_4$ |
|---|---|---|---|---|---|
| 1:1 | Solid* | Highly viscous liquid* | Phase separation* | Solid* | Solid* |
| 1:2 | 144 | 1 | Solid* | Highly viscous liquid* | Liquid |
| 1:3 | Liquid | Liquid | Liquid | Liquid | Liquid |
| 1:4 | Liquid | Liquid | Liquid | Liquid | Liquid |
| 1:5 | Liquid | Liquid | Liquid | Liquid | Liquid |
| 1:6 | Liquid | Liquid | Liquid | Liquid | Liquid |
| 1:7 | Liquid | Liquid | Liquid | Liquid | Liquid |

TABLE 1-continued

Table 1
Observation results of state

| Molar ratio Base:Phosphoric acid | Example 1 4MI/$H_3PO_4$ | Example 2 1EI/$H_3PO_4$ | Example 3 DMCA/$H_3PO_4$ | Example 4 TEOA/$H_3PO_4$ | Example 5 BA/$H_3PO_4$ |
|---|---|---|---|---|---|
| 1:8  | Liquid | Liquid | Liquid | Liquid | Liquid |
| 1:9  | Liquid | Liquid | Liquid | Liquid | Liquid |
| 1:10 | Liquid | Liquid | Liquid | Liquid | Liquid |
| 1:11 | Liquid | Liquid | Liquid | Liquid | Liquid |
| 1:13 | Liquid | Liquid | Liquid | Liquid | Liquid |
| 1:15 | Liquid | Liquid | Liquid | Liquid | Liquid |
| 1:19 | Liquid | Liquid | Liquid | Liquid | Liquid |
| 1:24 | Liquid | Liquid | Liquid | Liquid | 3 |
| 1:34 | 10 | 72 | Liquid | 24 | Liquid |
| 1:49 | 24 | Liquid | 1 | Liquid | Liquid |
| 1:99 | 1 | 72 | 24 | 30 | 24 |

Symbol "*" denotes the state at room temperature, the others are at −30° C.

The numerical values show the time elapsed (in hours) at which the electrolyte is apparently confirmed to completely solidify (observed for one month).

Synthesis Example 1

In a four-necked separable flask equipped with a stirrer, a nitrogen inlet tube, and an exhaust tube, were charged N,N-dimethylacetamide, as a solvent, and 4,4'-diaminodiphenyl ether and 3,3'-dihydroxy-4,4'-diaminobiphenyl in a molar ratio of 6/4, as the diamine components, and the mixture was stirred at 40° C. in a nitrogen atmosphere for dissolution. Here was added 3,3',4,4'-biphenyltetracarboxylic dianhydride in an equimolar amount with respect to the diamine components by portions in several steps, and the reaction was performed at 40° C. for about 12 hours to obtain a viscous solution of polyamic acid with a solid content of 9.0 wt %. This solution was cast on a SUS plate with a mirror-polished surface. The cast film was covered with a polyolefin microporous membrane (UP-3025; manufactured by Ube Industries, Ltd.) to regulate the solvent replacing speed, and the laminate was immersed in methanol and then in water to obtain a polyamic acid microporous membrane. The periphery of the membrane was fixed with a pin tenter and heat-treated at 320° C. in the air to obtain polyimide microporous membrane PI-1 having the following properties.

Tg: 290° C.
Average pore diameter: 0.12 μm
Porosity: 68%
Thickness: 76 μm
Linear expansion coefficient: $4.634 \times 10^{-5}$/° C.

Here, the above properties were determined by the following methods.

1) Porosity:

The thickness and weight of the microporous membrane cut into a predetermined size were measured. The porosity of the porous film was calculated from the basis weight using the following equation. In the equation, S is the area of the microporous membrane, d is the thickness, w is the weight measured, and D is the density of polyimide, which is assumed 1.34 here.

Porosity=$(1-w/(S \times d \times D)) \times 100$

2) Average Pore Diameter:

The micropore diameter was measured in the range of 3.4 nm to 400 μm with a mercury intrusion porosimeter AUTOSCAN-60+500 manufactured by Yuasa Ionics Inc. The average value over the range of 3.4 nm to 1 μm was obtained.

3) Linear Expansion Coefficient

Linear expansion coefficient was measured with TMA-50 manufactured by Shimadzu Corporation in a nitrogen atmosphere in the course of heating from 50° C. to 200° C. at 20° C./min.

4) Tg

Tg was determined from the temperature dispersion profiles of dynamic viscoelasticity and loss tangent measured with Rheometrics RSAII in a tensile mode at a frequency of 5 Hz with 0.1%-strain in the course of heating from −50° C. to 500° C. at 3° C./min.

Example 12

Composite Electrolyte Membrane Using 4-methylimidazole/phosphoric Acid (4MI/$H_3PO_4$) Liquid Electrolyte In a petri dish, polyimide microporous membrane PI-I 50 mm×50 mm in size prepared in Synthesis Example 1 was immersed in 4MI/$H_3PO_4$ 1:19 liquid electrolyte prepared in Example 1, and the system was kept under reduced pressure at 90° C. for 2 hours. Then, the liquid electrolyte adhered on both surfaces of the membrane was wiped off with a powder paper. After this impregnation, the specimen turned into deep color, suggesting retention of the liquid electrolyte in the micropores. The ionic conductivities of this composite electrolyte membrane using 4MI/$H_3PO_4$ 1:19 liquid electrolyte were $0.8 \times 10^{-3}$ $Scm^{-1}$ at −30° C. and $1.0 \times 10^{-1}$ $Scm^{-1}$ at 150° C. In contrast to the composite electrolyte membrane described below in Comparative Example 2, which exhibited drastic decrease in the ionic conductivity with the solidification at low temperatures, the composite electrolyte membrane using 4MI/$H_3PO_4$ 1:19 liquid electrolyte did not solidify and retained a high ionic conductivity.

With the above composite electrolyte membrane comprising 4MI/$H_3PO_4$ 1:19 liquid electrolyte, power generation was tested at 120° C. at a gas flow rate of 150 ml/min for hydrogen and oxygen, using a fuel cell FC25-02SP and a gas diffusion electrode EC-20-10-10 manufactured by Electrochem, Inc. It was confirmed that the fuel cell can generate electric power.

Example 13

Composite Electrolyte Membrane Using N,N-diethylmethylamine/phosphoric Acid (DEMA/$H_3PO_4$) Liquid Electrolyte A composite electrolyte membrane composed of DEMA/$H_3PO_4$ 1:3 liquid electrolyte and the polyimide microporous membrane was obtained similarly to Example 12 except that a methanol solution containing 60 wt % of DEMA/$H_3PO_4$ 1:3 liquid electrolyte obtained in Example 6 was used and that the system was kept under reduced pressure, at first, at room temperature for 12 hours and then at 90° C. for 2 hours. The ionic conductivities of the resulting composite electrolyte membrane were $1.1 \times 10^{-6}$ Scm$^{-1}$ at −30° C. and $0.3 \times 10^{-1}$ Scm$^{-1}$ at 150° C. The liquid electrolyte did not solidify.

Example 14

Composite Electrolyte Membrane Using 1-methylpyrrolidine/phosphoric Acid (1MP/$H_3PO_4$) Liquid Electrolyte A composite electrolyte membrane composed of 1 MP-$H_3PO_4$/1:3 liquid electrolyte and the polyimide microporous membrane was obtained similarly to Example 13 except that 1MP/$H_3PO_4$ 1:3 liquid electrolyte prepared in Example 10 was used instead of DEMA/$H_3PO_4$ 1:3 liquid electrolyte. The resulting composite electrolyte membrane exhibits an ionic conductivity of $0.8 \times 10^{-1}$ Scm$^{-1}$ at 150° C.

Comparative Example 2

Composite Electrolyte Membrane Using Phosphoric Acid

Crystalline phosphoric acid was dissolved in methanol in a concentration of 30 wt %, and a composite electrolyte membrane was obtained similarly to Example 13 with this solution. The ionic conductivities of this composite electrolyte membrane were $0.1 \times 10^{-4}$ Scm$^{-1}$ at −30° C. and $2.1 \times 10^{-1}$ Scm$^{-1}$ at 150° C. Below 20° C., phosphoric acid solidified, thereby the ionic conductivity drastically decreased.

Industrial Applicability

The present invention provides a novel ion-conductive or proton-conductive liquid electrolyte that comprises a base and phosphoric acid and remains liquid even at −30° C.; and a composite electrolyte membrane that is composed of the liquid electrolyte and a porous body, dose not solidify at low temperatures, and exhibits high ionic conductivity at both low and high temperatures even without water or solvent added. The present liquid electrolyte and composite electrolyte membrane can be used for fuel cells, secondary batteries, electrical double layer capacitors, electrolytic capacitors, and the like.

What is claimed is:

1. A liquid electrolyte for a phosphoric acid fuel cell, comprising a base A and phosphoric acid B, wherein:
   the electrolyte has a molar ratio, A:B, in a range of 1:3 to 1:50;
   the electrolyte has an ionic conductivity of $10^{-6}$ Scm$^{-1}$ or more at −30° C.;
   the electrolyte has an ionic conductivity of $10^{-2}$ Scm$^{-1}$ or more at 150° C.;
   the base is a pyrrolidine represented by chemical formula (3):

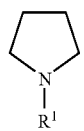

(3)

wherein R$^1$ is a hydrocarbon group having 1 to 20 carbon atoms or a hydrogen atom, and
the temperature at which said electrolyte solidifies is lower than −30° C.

2. The liquid electrolyte according to claim 1, wherein the liquid electrolyte is a proton conductor.

3. A fuel cell comprising the liquid electrolyte according to claim 1.

4. A composite electrolyte membrane comprising a porous body impregnated with the liquid electrolyte according to claim 1.

5. A fuel cell comprising the composite electrolyte membrane according to claim 4.

* * * * *